(12) United States Patent
Santambrogio (10) Patent No.: US 11,712,425 B2
(45) Date of Patent: Aug. 1, 2023

(54) IMMUNOREGULATORY ROLE OF 3-OH-KYNURENAMINE AND USES THEREOF

(71) Applicant: ALBERT EINSTEIN COLLEGE OF MEDICINE, Bronx, NY (US)

(72) Inventor: Laura Santambrogio, New York City, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 355 days.

(21) Appl. No.: 16/980,204

(22) PCT Filed: Mar. 12, 2019

(86) PCT No.: PCT/US2019/021731
§ 371 (c)(1),
(2) Date: Sep. 11, 2020

(87) PCT Pub. No.: WO2019/178013
PCT Pub. Date: Sep. 19, 2019

(65) Prior Publication Data
US 2021/0008021 A1    Jan. 14, 2021

Related U.S. Application Data (60) Provisional application No. 62/642,633, filed on Mar. 14, 2018.

(51) Int. Cl.
*A61K 31/198* (2006.01)
*A61P 37/00* (2006.01)
*A61K 38/21* (2006.01)

(52) U.S. Cl.
CPC .......... *A61K 31/198* (2013.01); *A61K 38/217* (2013.01); *A61P 37/00* (2018.01)

(58) Field of Classification Search
None
See application file for complete search history.

(56) References Cited

U.S. PATENT DOCUMENTS

| | | | |
|---|---|---|---|
| 7,622,495 B2 | 11/2009 | Peleg-Shulman et al. | |
| 8,309,767 B2 | 11/2012 | Zisapel et al. | |
| 2002/0022032 A1* | 2/2002 | Curry | A61K 41/0057 424/183.1 |
| 2009/0297475 A1 | 12/2009 | Waring et al. | |
| 2012/0252896 A1* | 10/2012 | Ernst | A61K 31/40 514/567 |
| 2015/0182592 A1 | 7/2015 | Salford et al. | |

FOREIGN PATENT DOCUMENTS

WO    2016044922 A1    3/2016

OTHER PUBLICATIONS

Arreola et al. Journal of Immunology Research, vol. 2015;2015:354957. doi: 10.1155/2015/354957. (Year: 2015).*
PubChem Entry for 3-OH-kynurenamine [online], PubChem [retrieved on Mar. 6, 2023], Retrieved from the internet: <https://pubchem.ncbi.nlm.nih.gov/compound/3-Hydroxykynurenamine>. (Year: 2023).*
International Search Report and Written Opinion for International Application PCT/US2019/021731; International Filing Date: Mar. 12, 2019; dated Jun. 13, 2019; 6 pages.

* cited by examiner

*Primary Examiner* — Katherine Peebles
(74) *Attorney, Agent, or Firm* — Cantor Colburn LLP (57) ABSTRACT

Methods are provided for using 3-OH-kynurenamine to treat and prevent an inflammatory or autoimmune disease or disorder or transplant rejection, and for promoting immune tolerance.

3 Claims, 10 Drawing Sheets

IMMUNOREGULATORY ROLE OF 3-OH-KYNURENAMINE AND USES THEREOF

CROSS REFERENCE TO RELATED APPLICATIONS

This application is a National Stage application of PCT/US2019/021731, filed Mar. 12, 2019, which claims the benefit of U.S. Provisional Application No. 62/642,633, filed Mar. 14, 2018, both of which are incorporated by reference in their entirety herein.

BACKGROUND OF THE INVENTION

Tryptophan (Trp) catabolism plays a major role in the modulation of immune responses (1-3). By metabolizing Trp, and thus depleting an essential amino acid required for protein synthesis and proliferation, dendritic cells (DCs) strongly inhibit T cell proliferation (5). Additionally, metabolites from the Trp pathway are immunosuppressive in several experimental models of autoimmunity and chronic inflammation by activating the aryl hydrocarbon receptor (AhR), thus favoring the generation of regulatory dendritic cells and regulatory T cells (Treg) (6-8).

Trp catabolism can generate different metabolites in different cells (11-14). In fact, besides being the precursor of well-known serotonin and melatonin, Trp is the main substrate of indoleamine 2,3-dioxygenase 1 (IDO1), the rate-limiting enzyme in the kynurenine pathway that includes several downstream enzymes and thus generates a sequential cascade of metabolites, collectively known as kynurenines (L-kynurenine, 3-OH-L-kynurenine, 3-OH-anthranilic acid, quinolinic acid, and kynurenic acid) (15). The kynurenine pathway has been well characterized in dendritic cells and macrophages, in which up-regulation of IDO1 expression, induced by the cytokine interferon-γ (IFN-γ) confers potent immunoregulatory properties (1,2,5,7). These effects derive by depletion of Trp in the microenvironment of T cells and appearance of immunosuppressive kynurenines, among which L-kynurenine (the direct product of IDO1) is known to favor the activity of regulatory T (Treg) cells by acting as an agonist of the arylhydrocarbon receptor (AhR) (16-18).

Differently from Kynurenine (which still share the amino and carboxyl groups with their Trp precursor), Kynurenamines lack the carboxyl group and thus are not kynurenines but biogenic amines. This large family of biogenic amines is still poorly characterized. Among these, 5-OH-kynurenamine has been known to be produced by Trp catabolism in the brain, liver, pineal gland and smooth muscle cells. 5-OH-Kynurenamine functions as a vasopressor likely through its binding to serotonin receptors (31). Kynurenamines can also derive from melatonin catabolism, where cleavages of the indole ring by the indole 2,3 deoxygenase generates N-formyl-N-acetyl-5-methoxy kynurenamine. This substrate is further metabolized by the action of formamidase to generate N-acetyl-5-methoxy kynurenamine. Both these metabolites have the ability to inhibit prostaglandin generation (32). Additionally, kynurenamine derivatives modified by urea or thiourea moiety, such as 1-13-(2-amino-5-chlorophenyl)-3-oxopropyl1-3-ethylurea, have been shown to inhibit iNOS and eNOS, producing inflammatory nitric oxide (NO). Interestingly, by binding IDO1 heme, NO is a physiologic inhibitor of Trp catabolism, suggesting an important bidirectional influence between IDO1— and NOS-mediated pathways. N1-acetyl-5-methoxykynurenamine has been shown to be produced by epithelial cells and to have a strong antiproliferative effect on different cell lines (33).

Kynurenamine derivatives have been shown to function as vasopressor (5-OH-Kynurenamine) inhibitors of prostaglandin formation (N-acetyl-5-methoxy kynurenamine), inhibitors of iNOS/eNOS (ethylurea-kynurenamine derivatives) and inhibitors of cell proliferation (N1-acetyl-5-methoxykynurenamine) (31-33).

The present invention addresses the need for improved agents for treating and preventing autoimmune and inflammatory diseases and disorders.

SUMMARY OF THE INVENTION

Methods are provided for treating and preventing an inflammatory or autoimmune disease or disorder, for treating or preventing transplant rejection, and for promoting immune tolerance, comprising administering 3-OH-kynurenamine, and/or an agent that promotes secretion of 3-OH-kynurenamine, to a subject in need thereof.

Also provided is a pharmaceutical composition comprising 3-OH-kynurenamine and a pharmaceutically acceptable carrier.

BRIEF DESCRIPTION OF THE DRAWINGS

FIG. 2. 3-OH-kynurenine is converted to 3-OH-kynurenamine by AADC. Tryptophan, a natural substrate for aromatic L-amino acid decarboxylase (AADC) was incubated with the enzyme and the PLP catalyst. In a separate reaction 3-OH-kynurenine was incubated under the same experimental conditions. Reactions were monitored over a 40 min. period. Trp was converted to Tryptamine (positive control). Similarly, 3-OH-kynurenine was converted to 3-OH-kynurenamine, indicating that AADC is likely the enzyme generating the same reaction in LEC. One of a triplicate experiment is shown.

DETAILED DESCRIPTION OF THE INVENTION

The present invention provides a method for treating or preventing an inflammatory or autoimmune disease or disorder, for treating or preventing a transplant rejection, or for promoting immune tolerance in a subject in need thereof, the method comprising administering to the subject 3-OH-kynurenamine in an amount effective to treat or prevent an inflammatory or autoimmune disease or disorder, treat or prevent a transplant rejection, or promote immune tolerance in a subject.

The invention also provides a method for treating or preventing an inflammatory or autoimmune disease or disorder, for treating or preventing a transplant rejection, or for promoting immune tolerance in a subject in need thereof, the method comprising administering to the subject an agent that promotes secretion of 3-OH-kynurenamine from lymphatic endothelial cells in an amount effective to treat or prevent an inflammatory or autoimmune disease or disorder, treat or prevent a transplant rejection, or promote immune tolerance in a subject.

The agent that promotes secretion of 3-OH-kynurenamine from lymphatic endothelial cells can be, for example, interferon gamma. In cases where interferon gamma is used, the subject does not have a disease or disorder where interferon gamma is already known to be useful in treating the disease or disorder, such as, for example, chronic granulomatous disease, osteopetrosis, idiopathic pulmonary fibrosis, Friedreich's ataxia, atopic dermatitis, or cancer, including bladder carcinoma, ovarian carcinoma and melanoma.

The inflammatory disease or disorder can be, for example, one or more of acute inflammatory disease, chronic inflammatory disease, acne vulgaris, asthma, atherosclerosis, auto-inflammatory disease, celiac disease, chronic prostatitis, colitis, diverticulitis, glomerulonephritis, hidradenitis suppurativa, inflammatory bowel disease, interstitial cystitis, lichen planus, mast cell activation syndrome, mastocytosis, otitis, pelvic inflammatory disease, reperfusion injury, rheumatic fever, rheumatoid arthritis, rhinitis, sarcoidosis, transplant rejection and vasculitis.

The autoimmune disease or disorder can be, for example, one or more of celiac disease, diabetes mellitus type 1, Graves' disease, inflammatory bowel disease, multiple sclerosis, psoriasis, rheumatoid arthritis, and systemic lupus erythematosus.

As used herein, to "treat" a disease or disorder means to alleviate a sign or symptom of the disease or disorder. As used herein, to "prevent" a disease or disorder means to reduce the likelihood of occurrence of the disease or disorder.

3-OH-kynurenamine can be administered to subjects using routes of administration known in the art. The administration can be systemic or localized to a specific site. Routes of administration include, but are not limited to, intravenous, intramuscular, intrathecal or subcutaneous injection, transdermal, oral and rectal administration, and injection into a specific site.

Also provided is a pharmaceutical composition comprising 3-OH-kynurenamine and a pharmaceutically acceptable carrier. Pharmaceutically acceptable carriers are well known in the art. Pharmaceutically acceptable carriers that can be used herewith encompasses any of the standard pharmaceutical carriers or diluents, such as, for example, sterile isotonic saline, phosphate buffered saline solution, water, and emulsions, such as an oil/water or water/oil emulsions.

The pharmaceutical compositon can comprise 3-OH-kynurenamine in a dosage amount effective to treat or prevent an inflammatory or autoimmune disease or disorder, treat or prevent a transplant rejection, or promote immune tolerance in a subject.

This invention will be better understood from the Experimental Details, which follow. However, one skilled in the art will readily appreciate that the specifics discussed are merely illustrative of the invention as described more fully in the claims that follow thereafter.

Experimental Details

The scientific premises for this invention generate from the observation that Trp metabolites are present in the lymph of healthy mice that led us to discover that Lymphatic Endothelial Cells (LEC):

express indoleamine 2,3-dioxygenase 1 (IDO1), the key, rate-limiting enzyme in Trp catabolism along the kynurenine pathway, produce metabolites of the Trp catabolism pathway (3-OH-kynurenamine) that were not previously observed in dendritic cells and macrophages, or other mammalian cells where Trp catabolism has been analyzed extensively, through the action of Aromatic Amino Acid Decarboxylase, secrete 3-OH-kynurenamine and LEC-secreted 3-OH-kynurenamine confers immunosuppressive properties to dendritic cells.

Metabolomic analysis of LEC under resting or IFN-y stimulation determined that in these cells the most abundant among the Trp metabolites is 3-OH-kynurenamine, a "lateral" product of 3-OH-kynurenine along the main branch of the kynurenine pathway (FIG. 1). These data are particularly exciting since this metabolite was never reported among the ones observed in dendritic cells and macrophages or in vasal endothelial cells, suggesting that LEC cells may have a "lateral" kynurenine pathway favoring the production of an alternative Trp metabolite. Additionally, no known function for this metabolite has been reported in the literature and an NCBIPubChem compound search did not produce 3-OH-Kynurenamine.

Determination of the enzyme responsible for 3-OH-kynurenamine production. Generation of 3-OH-kynurenamine from 3-OH-L-kynurenine requires a reaction of decarboxylation, The protease family of decarboxylase includes 20 members, among which the aromatic amino acid decarboxylase (AADC protease #4.1.1,28) is already known to be involved in two steps of Trp catabolism: conversion of 5-OH-L-kynurenine into 5-OH-kynurenamine and conversion of 5-OH-L-Trp into serotonin. As a first step, it was investigated whether this enzyme was present in LEC. Thus, Western blot (WB) analysis of LEG lysates was performed. Tissue known to express this enzyme (brain, heart, kidney) was used as positive controls. LEC were indeed determined to express AADC. Due to RNA splicing, several isoforms exist of AADC; so far the longest isoform has been cloned in the brain and the shortest in the kidney (34). WB analysis performed in LEC detected 3 separate bands within the 40 to 60 kDa molecular weight range. To determine whether any of these bands could be related to differential glycosylation, LEC lysates were treated with a mixture of EndoH/F enzymes to remove all the sugar groups. The band around 58 kDa disappeared following EndoH/F treatment and only two bands remained (around 55 and 43 kDa). Thus, by WB analysis, it appears that LEC express two AADC isoforms. The presence of AADC was also confirmed by immunofluorescence on cultured LEC.

Figure 1A:
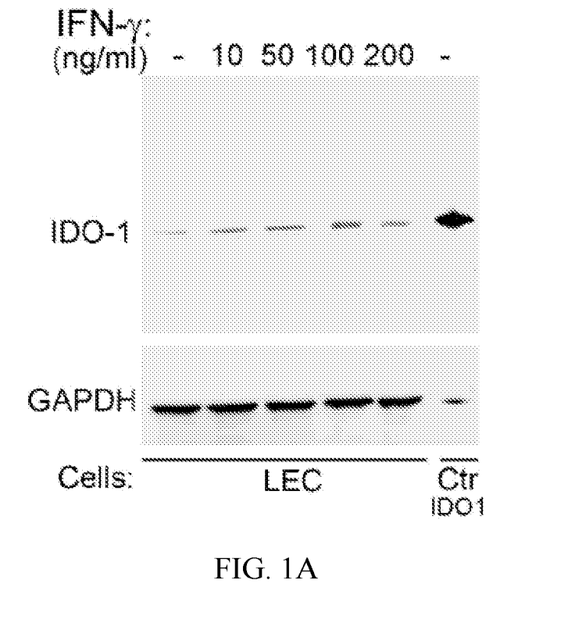
FIG. 1A-1D. A) IDO1, the key enzyme in tryptophan catabolism is expressed in primary lymphatic endothelial cells. B, C, D) Tryptophan metabolites in lymphatic endothelial cells (LEC). LEC were cultured in serum free media for 24 or 48 hours with either TGFβ (10 ng/ml), IL-4 (5 ng/ml), IFNγ (100 ng/ml) or no cytokines (Ctr). Culture supernatant was then collected and the metabolites analysed using targeted metabolomics analysis. Data were normalized to media alone. Data are reported as average±SD of quadruplicate experiments. Only (C) lymphatic endothelial cells but not (D) Dendritic Cells produce 3-OH-Kynurenamine, a lateral metabolite in (B) Tryptophan metabolism.
Figure 1B:
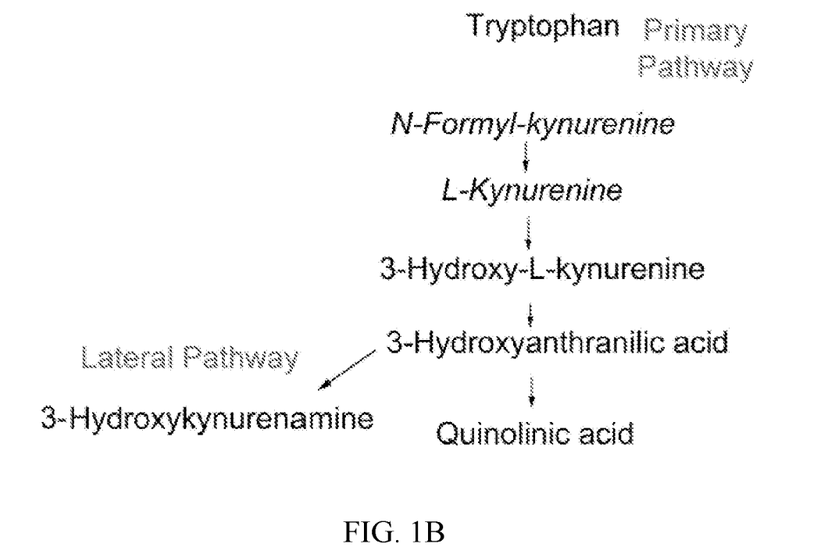
Figure 1C:
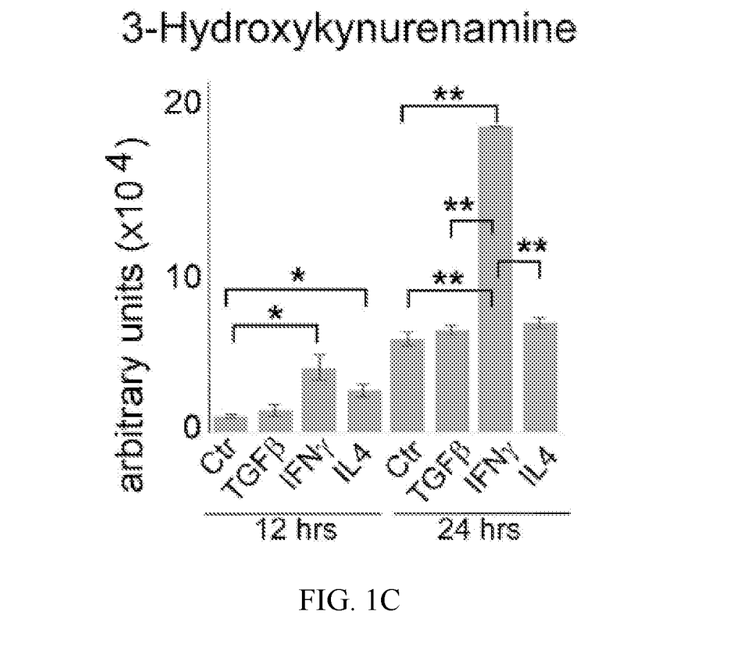
Figure 1D:
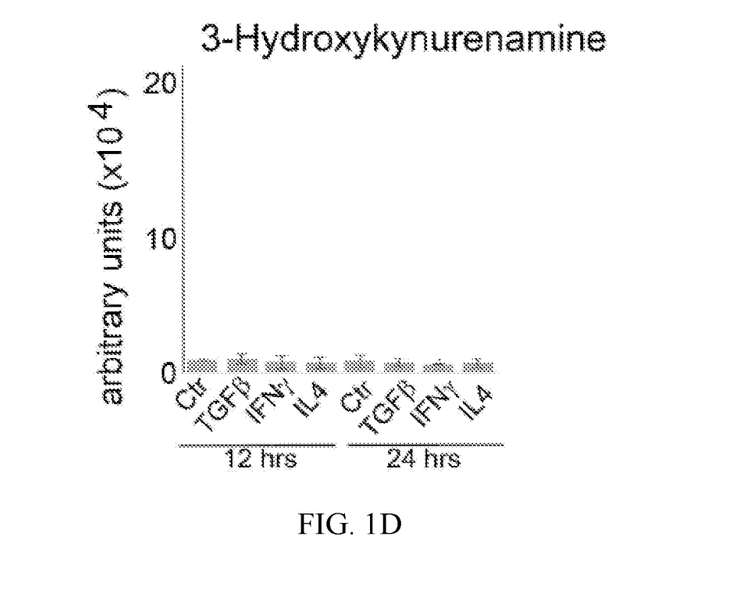
Figure 2:
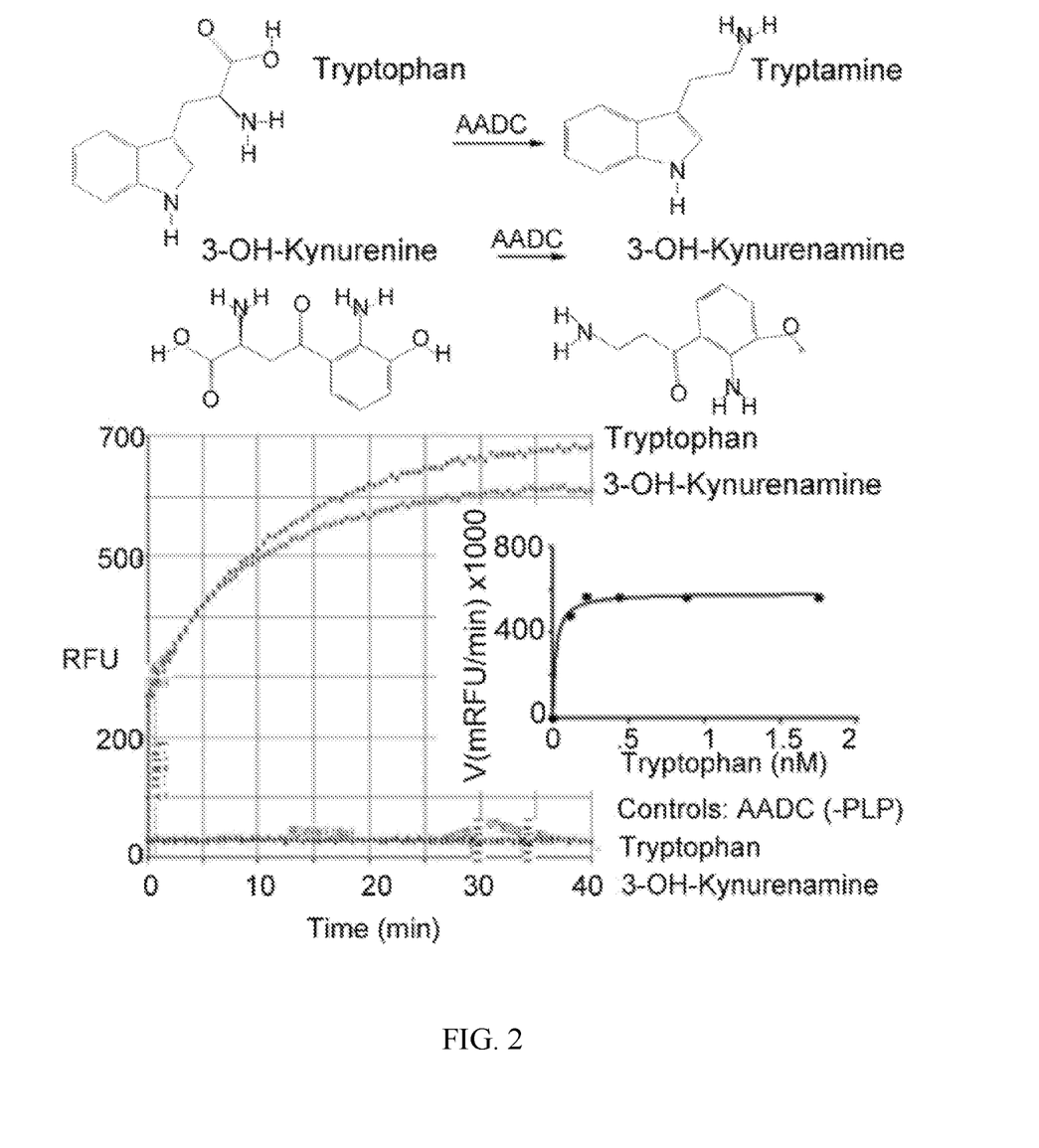
Figure 3A:
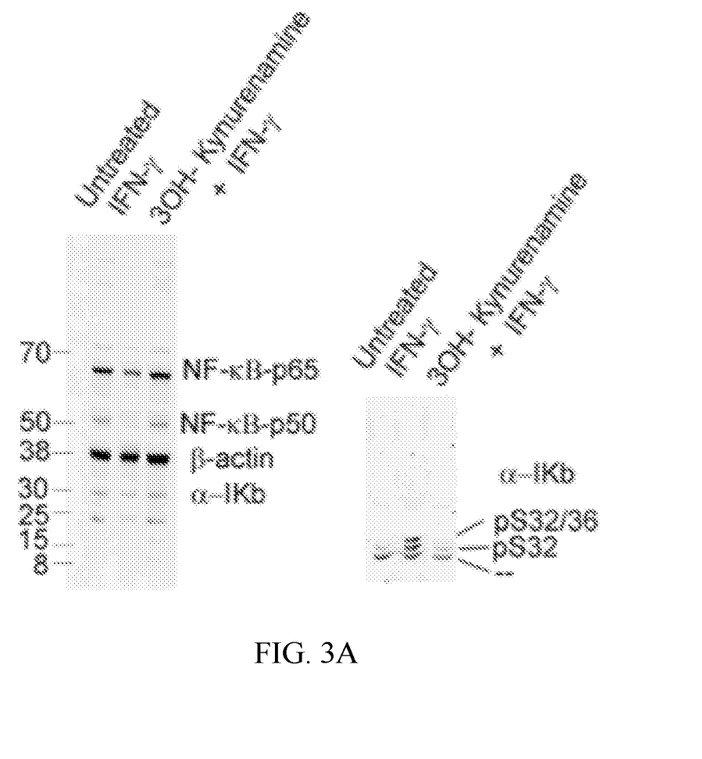
FIG. 3A-3D. 3-OH-kynurenamine confers immunosuppressive properties on DCs. A) Western blot and B) densitometric statistical analysis of 3-OH-Kynurenamine down-regulation of the NFκB pathway. Analysis (B) was calculated from 3 independent experiments. C and D) mouse cDCs (C) and human PBMCs (D). After incubation with 30 (C) or 2 (D) μM kynurenines, gene expression was evaluated by RT-PCR at 6– (C) or 6 and 18 (D) h. Data were normalized to GAPDH expression and presented relative to results in untreated cells (dotted line, one-fold). Mean fold induction+SD of triplicate experiments.
Figure 3B:
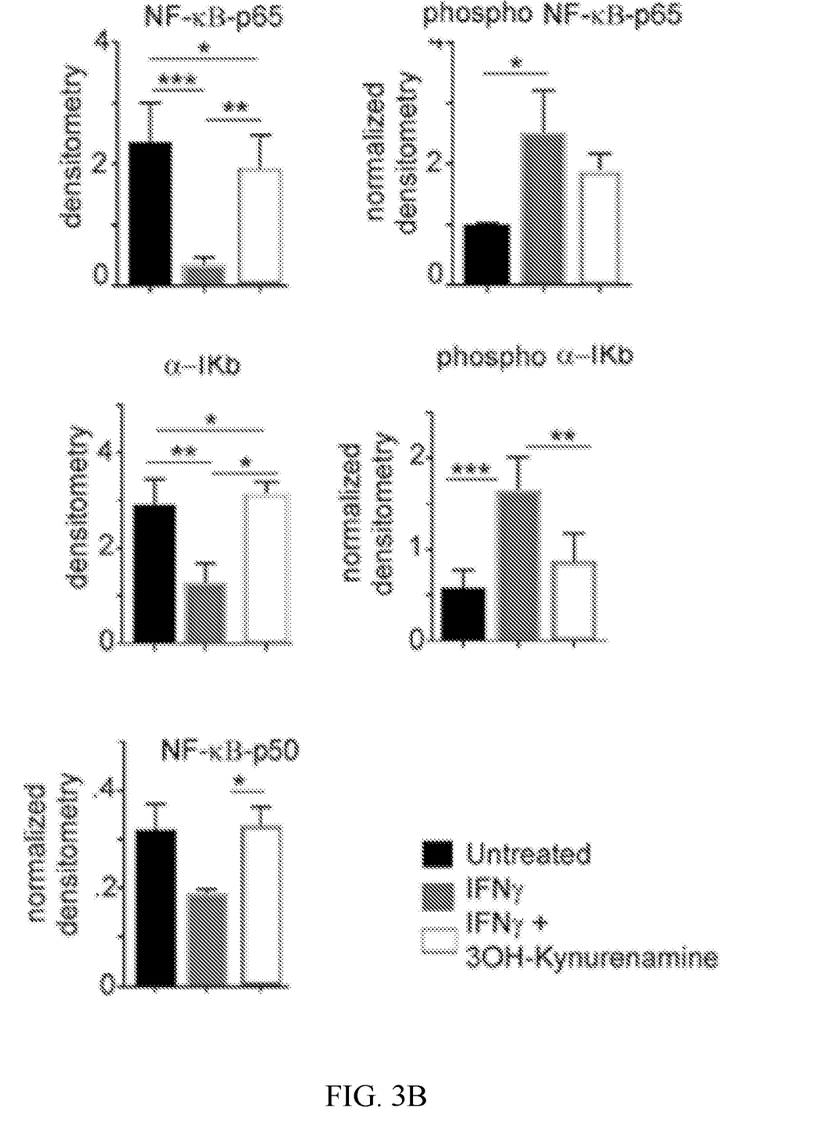
Figure 3C:
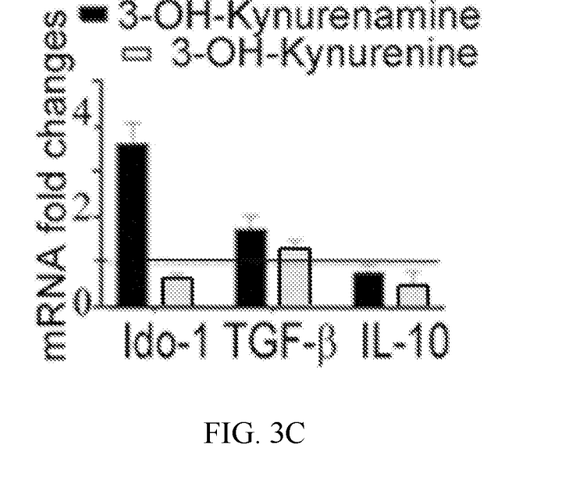
Figure 3D:
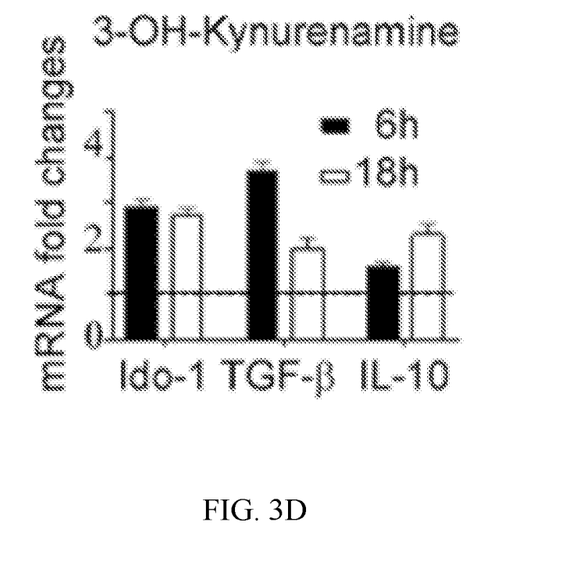

As a next step, to determine whether AADC is the natural enzyme processing 3-OH-L-kynurenine into 3-OH-kynurenamine, full-length recombinant AADC was incubaled with 3-OH-kynurenine and its conversion to 3-OH-kynurenamine was followed by detecting $CO_2$ production due to decarboxylation. A known substrate for AADC is tryptophan, converted to tryptamine, which was used as positive control in this reaction (FIG. 2). As shown over a real-time 40-min measurement, AADC was capable of inducing 3-OH-kynurenine decarboxylation; indicating that, at least in vitro, ADCC can generate 3-OH-kynurenamine.

Determination of 3-OH-kynurenamine receptor/molecular targets. The only known target for Trp metabolites is the Aryl Hydrocarbon receptor (AhR) (6,17,18). AhR is a transcription factor activated by several exogenous and endogenous ligands (39). Initially recognized as the receptor mediating the toxic effects of 2,3,7,8-tetrachlorodibenzo-p-dioxin, AhR is now considered as an important modulator of cell physiology and organ homeostasis (40). AhR expression is essentially ubiquitous in mammals, compatible with its broad spectrum activity. However, the nature of the AhR ligand, as well as the cell type expressing AhR, will ultimately dictate the AhR signaling pathway and the overall outcome of this activation (6). Among several physiologic effects, AhR contributes to immune homeostasis, by promoting immunoregulatory and host-protective effects (40). In dendritic cells, AhR activation by L-kynurenine up-regulates IDO1 expression, inducing an immunosuppressive circuitry loop (8).

To determine whether 3-OH-Kynurenamine could be a potential AhR ligand, experiments were performed using mouse embryonic fibroblasts (MEFs) constitutively expressing AhR and transfected with a firefly luciferase reporter plasmid containing an upstream promoter of mouse Cyp1a1 (a gene upregulated by AhR activation). Cells were either untreated or stimulated for 24 hours with different concentrations of 3-OH-kynurenamine and, as positive control, L-kynurenine, the known AhR agonist. L-kynurenine activated AhR in a concentration-dependent manner (FIG. 3). Interestingly, 3-OH-kynurenamine also induced a concentration-dependent AhR activation, around 6.5 times higher than L-kynurenine.

Figure 4A:
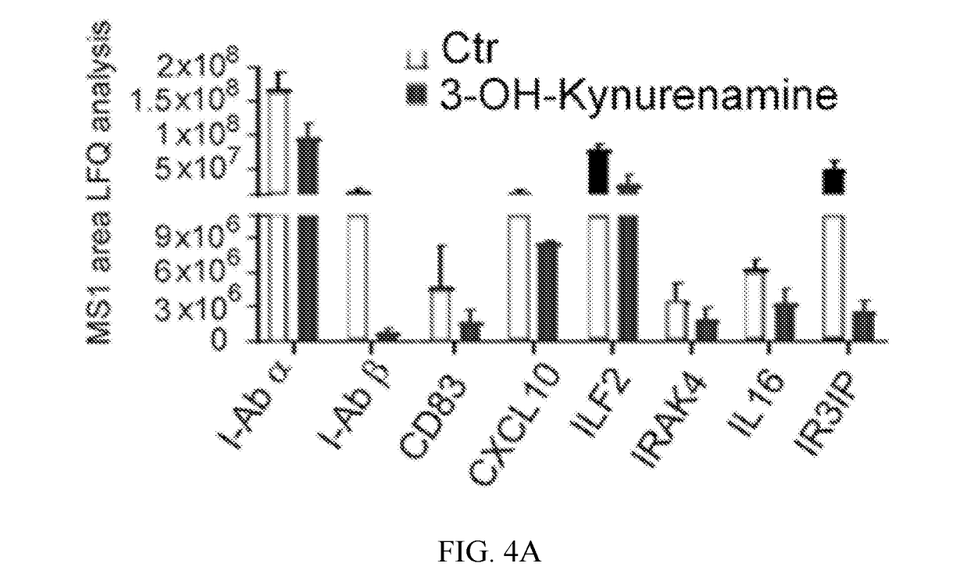
FIG. 4A-4B. A) MS1 quantification of immunological relevant proteins down-regulated following dendritic cells incubation with media alone (Ctr) or media supplemented with 3-OH-Kynurenamine. B) In vivo suppressive activity of CD8⁻ DCs, pulsed with the IGRP peptide (an autoantigen in autoimmune diabetes), in combination with a minority fraction (5%) of CD8⁻ DCs either untreated (Unt) or pretreated with 30 μM 3-OH-kynurenamine for 24 h and pulsed with the same peptide prior in vivo administration; analysis of skin reactivity of recipient mice to the eliciting peptide at 15 days is presented as change in footpad weight. ***$P<0.001$ (mean weight of experimental versus control footpads, i.e., injected with vehicle alone). Results are presented as fold induction±SD of triplicate experiments.
Figure 4B:
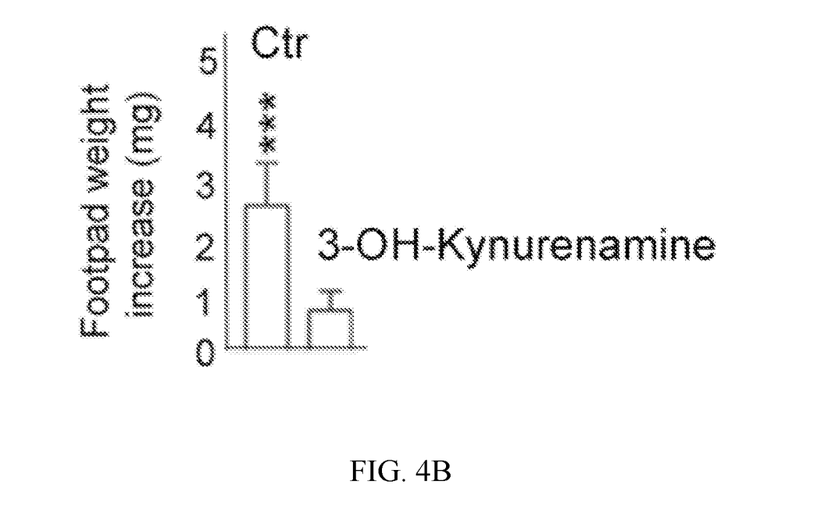
Figure 5A:
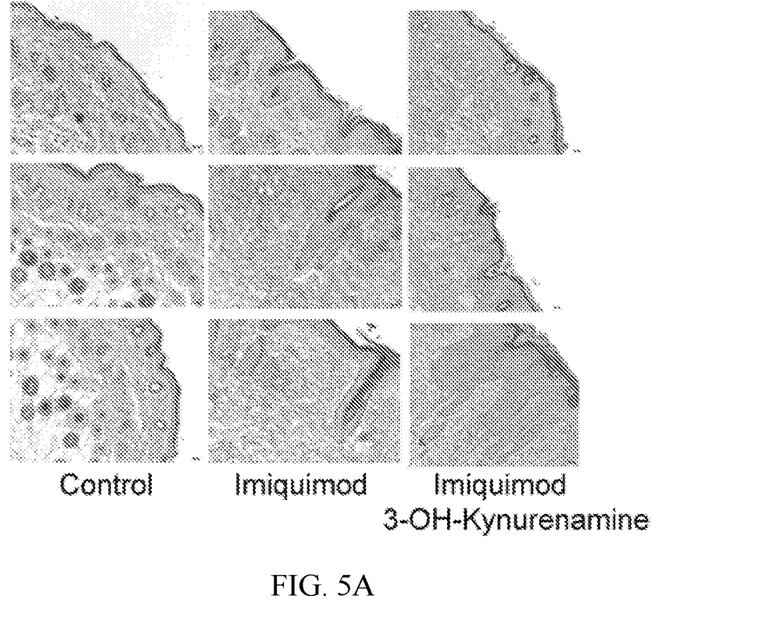
FIG. 5A-5B. 3-OH-Kynurenamine treatment decreases clinical and histological manifestation of psoriasis. a\A) Psoriasis was induced by shaving a 1"×1" area on the back and applying the TLR7 agonist Imiquimod for 7 days. Some of the mice were also treated with 3-OH-Kynurenamine (50 mg/kg ip; for 7 days). Controls are mice that were shaved but left untreated; Imiquimod and Imiquimod plus 3-OH-Kynurenamine refers to the specific treatments. After 7 days mice were sacrificed and skin processed for H&E staining. B) 3-OH-Kynurenamine treated mice presented a statistically significant lower levels or ortho and parakeratosis, epidermis hyperplasia and rete ridges formation.
Figure 5B:
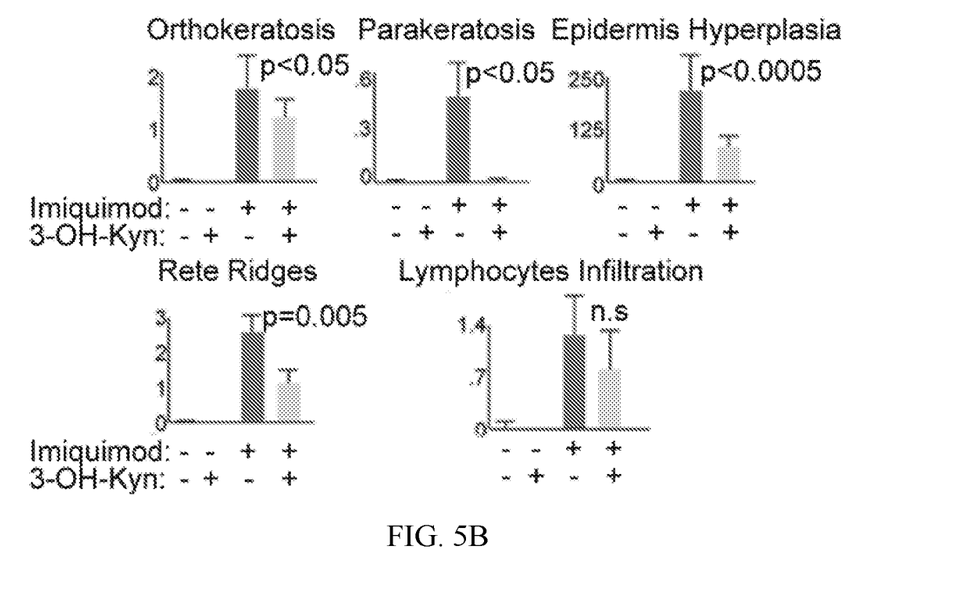
Figure 6A:
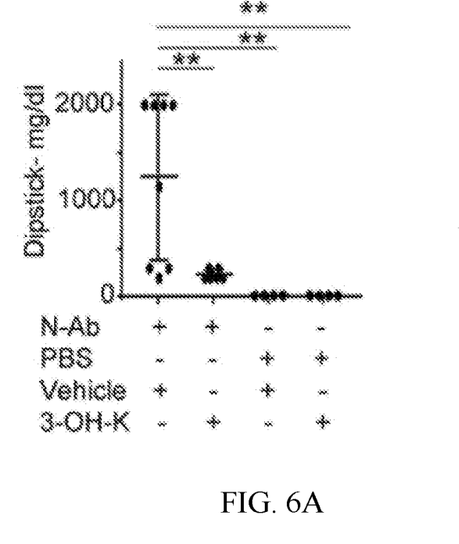
FIG. 6A-6F. Treatment with 3-OH-kynurenamine (3-OH-K)attenuates nephrotoxic nephritis (NTN). Ten week old female 129/Sv mice were immunized intraperitoneally with rabbit IgG in complete Freund's adjuvant (day 0). Five days later, mice received an intravenous injection of 90 ul of pre-formed rabbit anti-mouse glomerular basement membrane antibodies (N-Ab) or PBS. Starting at day +4, mice started receiving daily intraperitoneal injections of 50 mg/kg of 3-OH-kynurenamine (n=6) or vehicle control (n=8) until sacrifice on day +12. A) Proteinuria levels determined at sacrifice by uristix. B) % of mice in each group at sacrifice that reached the predetermined cut-off value for severe proteinuria of >300 mg/dl. C) Blood Urea Nitrogen levels determined at sacrifice. D) % of mice in each group that reach pre-specified humane end points for sacrifice (>300 mg/dl on two consecutive days, a single value of >2000 mg/dl, or poor general well being. E and F) All groups of mice developed similar titers of E) antirabbit injected Ab and F) anti-GBM Ab. These results indicate that 3-OH-kynurenamine did not interfere with model induction, and that differences in proteinuria were due to a specific effect of the molecule on kidney inflammation. (*$p<0.05$, **$p<0.01$).
Figure 6B:
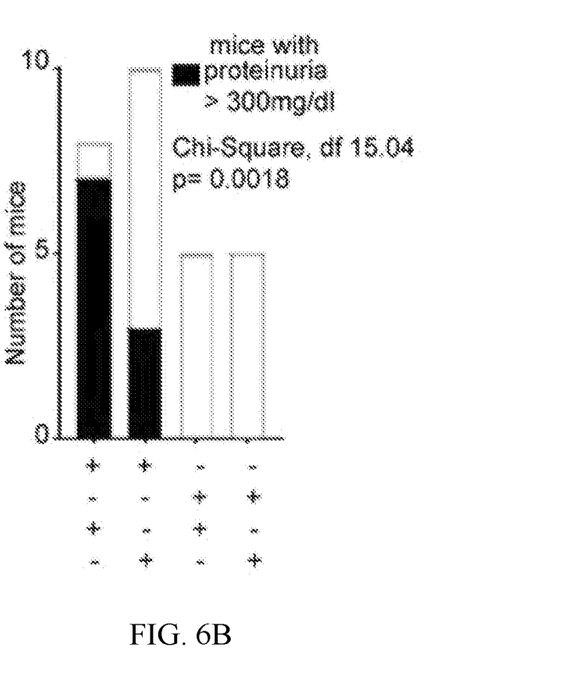
Figure 6C:
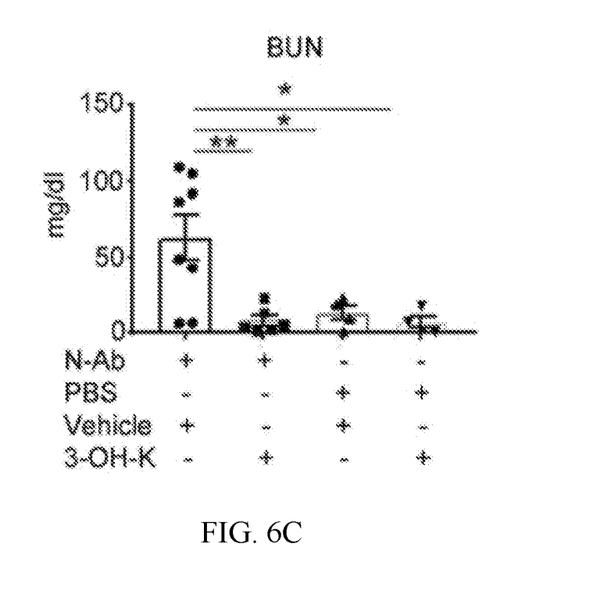
Figure 6D:
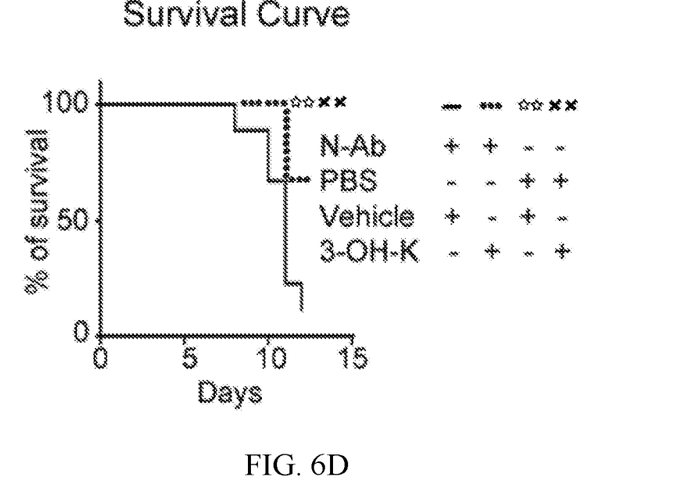
Figure 6E:
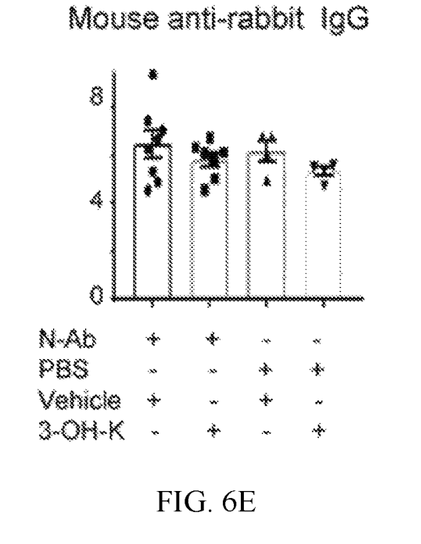
Figure 6F:
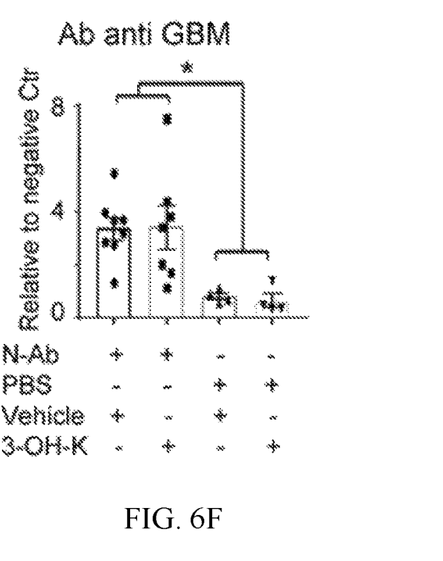

Biological Role of 3-OH-Kynurenamine. Trp metabolites are known to exert several functions in immune cells. In dendritic cells, either cDCs or pDCs, incubation with L-kynurenine and/or 3-OH-anthranilic acid induces IDO1 expression and production of immunosuppressive TGF-β production. In turn, cDCs and pDCs conditioned with these Trp catabolites increase differentiation of T lymphocytes into Treg cells in vitro and, when administered in vivo, induce antigen-specific T cell tolerance. Results indicated that conditioning of cDCs (purified from the spleens of conventional C57BL/6 mice) with 3-OH-kynurenamine at 30 µM significantly upregulates ido1 and Tgfb1 transcripts after 2-6 hr (FIG. 3). Moreover, cDCs conditioned with 3-OH-kynurenamine for 24 hr suppressed antigen-specific delayed-type hypersensitivity induced by untreated, immunostimulatory cDCs pulsed with a peptide mimicking a diabetogenic autoantigen (FIG. 4). Additionally, cDC treatment with 3-OH-kynurenamine (20 µM, 24 hr), followed by quantitative proteomic indicate up-regulation of the NF-κB inhibitor IKB in IFNγ/3-OH-kynurenamine treated cells as compared to IFNγ control (FIG. 4). In vivo animal models indicate that 3-OH-Kynurenamine decrease skin inflammation in a Psoriasis model (FIG. 5) and kidney damage, as tested by proteinuria and overall animal survival, in a model of nephrotoxic Lupus (FIG. 6).

What is claimed is:

1. A method for treating or preventing an autoimmune disease or disorder in a subject in need thereof, the method comprising administering to the subject 3-OH-kynurenamine in an amount effective to treat or prevent the autoimmune disease or disorder, wherein the autoimmune disease or disorder is psoriasis or nephrotoxic lupus.

2. The method of claim 1, wherein the subject does not have chronic granulomatous disease, osteopetrosis, idiopathic pulmonary fibrosis, Friedrich's ataxia, atopic dermatitis, bladder carcinoma, ovarian carcinoma or melanoma.

3. The method of claim 1, wherein the autoimmune disease or disorder is psoriasis.

* * * * *